(12) United States Patent
Degel et al.

(10) Patent No.: US 7,608,224 B2
(45) Date of Patent: Oct. 27, 2009

(54) STACK OF SUPPORTS, IN PARTICULAR FOR CRYOPRESERVATION OF BIOLOGICAL SAMPLES

(75) Inventors: Christian Degel, St. Ingbert (DE); Heiko Zimmermann, Kronberg im Taunus (DE); Günter R. Fuhr, Berlin (DE); Thomas Trautmann, Blieskastel (DE)

(73) Assignee: Fraunhofer-Gesellschaft zur Forderung der Angewandten Forschung e.V., Munich (DE)

( * ) Notice: Subject to any disclaimer, the term of this patent is extended or adjusted under 35 U.S.C. 154(b) by 502 days.

(21) Appl. No.: 10/564,491

(22) PCT Filed: Jul. 16, 2004

(86) PCT No.: PCT/EP2004/007956

§ 371 (c)(1),
(2), (4) Date: Mar. 3, 2006

(87) PCT Pub. No.: WO2005/007290

PCT Pub. Date: Jan. 27, 2005

(65) Prior Publication Data

US 2006/0154232 A1 Jul. 13, 2006

(30) Foreign Application Priority Data

Jul. 16, 2003 (DE) ................. 103 32 296

(51) Int. Cl.
*A01N 1/02* (2006.01)

(52) U.S. Cl. .......... 422/102; 422/99; 436/807; 436/809; 435/288.4

(58) Field of Classification Search ......... 422/101, 422/102; 435/305.1; 206/503, 512
See application file for complete search history.

(56) References Cited

U.S. PATENT DOCUMENTS

| | | | |
|---|---|---|---|
| 5,233,844 A | | 8/1993 | Knippscheer et al. |
| 6,699,437 B1 * | | 3/2004 | Astle .................. 422/102 |
| 6,878,344 B2 * | | 4/2005 | Mansky et al. .......... 422/101 |
| 2002/0051995 A1 | | 5/2002 | Kumar |
| 2004/0065093 A1 | | 4/2004 | Fuhr et al. |

FOREIGN PATENT DOCUMENTS

| | | |
|---|---|---|
| DE | 4300231 * | 12/1993 |
| DE | 4300231 C1 | 12/1993 |
| DE | 19752085 A1 | 6/1998 |
| DE | 10144925 A1 | 3/2003 |
| WO | 0221057 A1 | 3/2002 |

* cited by examiner

*Primary Examiner*—Jill Warden
*Assistant Examiner*—Dwan A Gerido
(74) *Attorney, Agent, or Firm*—Caesar, Rivise, Bernstein, Cohen & Pokotilow, Ltd.

(57) ABSTRACT

Substrates (100) are described for receiving a plurality of samples, especially for the preservation of biological samples at cryotemperatures comprising a plurality of substrate plates (11, 12, 13) arranged on top of one another as a stack (10) and comprising an anchoring axis (20) to which the substrate plates (11, 12, 13) are connected. Processes for the preservation of biological samples at cryotemperatures are also described.

27 Claims, 3 Drawing Sheets

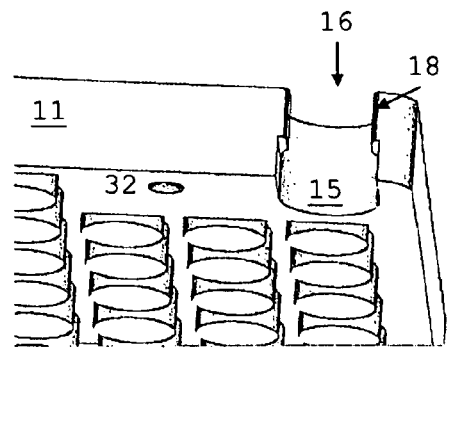
Fig. 4
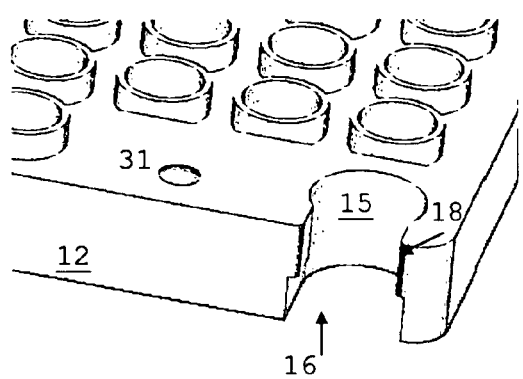
Fig. 5
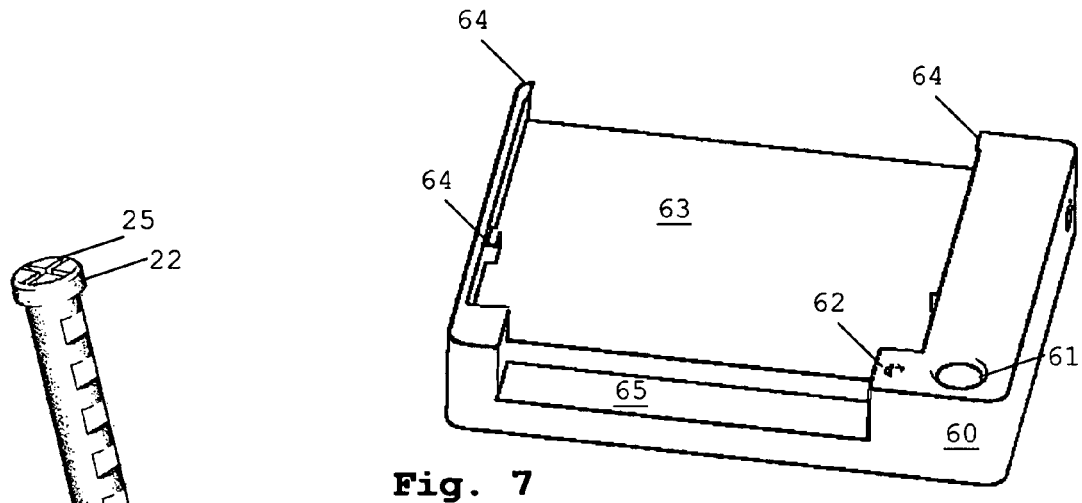
Fig. 6
Fig. 7
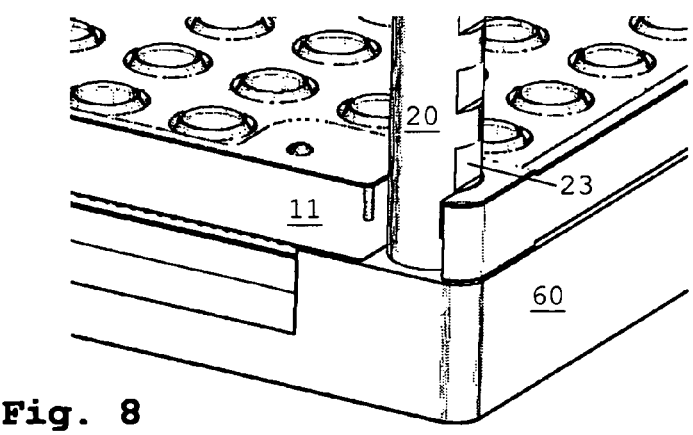
Fig. 8

STACK OF SUPPORTS, IN PARTICULAR FOR CRYOPRESERVATION OF BIOLOGICAL SAMPLES

BACKGROUND OF THE INVENTION

The invention relates to a substrate for receiving and storing a plurality of samples and in particular to a substrate for the cryopreservation of biological samples. The invention also relates to processes for the cryopreservation of samples with such a substrate.

The permanent storage in a frozen state (cryopreservation) of biological samples (especially biological tissue, tissue parts, biological cells, cellular groups, cell components, cellular organelles or biologically relevant macromolecules) is known. The biological samples are arranged in a dissolved or suspended state on a sample substrate that is transferred for cryopreservation into an environment with reduced temperature, e.g., into a cryotank.

Various forms of substrates for cryopreservation are known from practice that were developed on the basis of carrier systems in laboratory technology such as, e.g., from microtiter plates. Important requirements in the development of the conventional substrates for cryopreservation consisted in the making available of a high receiving capacity, in the adaptation to the freezing and storage conditions and in the flexibility and functionality of the substrate (ability to be easily adapted to certain preservation tasks, ability for samples to be more easily removed in the cryopreserved state). However, the conventional substrates (sample chambers) for cryopreservation can have the disadvantage that a compact arrangement, e.g., in a cryotank is associated with the danger of confusion.

For example, an unintended redistribution of substrates can occur in a cryocontainer that can only be corrected by expensive measures of data acquisition.

Another requirement for storage systems for cryopreservation is that an economical mass production should be possible. As regards this criterion, e.g., drawer systems for the ordered storing of substrates in cryocontainers would be disadvantageous since they have a complicated design and are limited in their ability to adapt to concrete preservation tasks.

The cited problems occur not only with substrates for holding samples for cryopreservation but in general in sample carriers for liquid (suspended or dissolved) or particulate samples of biological or synthetic origin for purposes of processing, reaction or storage.

The invention has the object of providing an improved substrate for receiving a plurality of samples with which the disadvantages of the conventional substrates (sample chambers) in particular for cryopreservation are overcome and that has in particular a compact design, can be mass-produced cost-effectively and makes possible a sample storage with reduced danger of confusion. Another object of the invention is the provision of improved processes for the cryopreservation of samples and in particular for supplying samples to or removing samples from a substrate in particular under cryotemperature conditions.

SUMMARY OF THE INVENTION

As concerns the device, the above-cited object is solved by the general technical teaching of providing a substrate for receiving a plurality of samples that comprises a stack compound consisting of a plurality of substrate plates. The substrate plates are detachably connected as partial substrates in a stack by at least one anchoring axis. The combination in accordance with the invention of individual substrate plates to a stack has the following advantages. The connection of the substrate plates to the anchoring axis defines the sequence of the substrate plates in the stack. An unintentional rearrangement of the substrate plates is excluded. Moreover, the substrates serve as mutual covering (closure function). This reliably prevents a mutual contamination of different samples. It is also advantageous that the substrate stack can be locked against unintended manipulations by the anchoring axis, which can consist of a single part. The substrate in accordance with the invention has a simplified design that can be completely produced from materials suitable for cryotemperatures and is suitable for an economical mass production.

The stack compound comprises at least two substrate plates (or palettes) of which at least one substrate plate is designed to receive samples. A substrate plate for receiving samples is generally a container or carrier in which or on which at least one sample is arranged in an exposed or covered manner. The geometric shape of the container or carrier can be selected to be different in dependence on the concrete tasks. For example, a substrate plate can contain one or several cup-shaped or elongated sample chambers.

The substrate plates are arranged on top of one another in the stack with a certain stack direction. The anchoring axis preferably runs parallel to the stack direction. If the substrate plates have a plane shape, the stack direction and the anchoring axis are correspondingly aligned perpendicular relative to the planes of the substrate plates. The anchoring axis preferably comprises a substantially rigid shape as structural component and is preferably bend-resistant, inherently stiff and stable also in a state without tensile stress. Preferably, precisely (exclusively) one anchoring axis is provided in particular for the pivoting of individual plates out of the stack.

According to a preferred embodiment of the invention each substrate plate comprises a bearing bore through which the anchoring axis passes. The bearing bores of the substrate plates and the anchoring axis form a bearing for the substrate plates so that a stable positioning of the substrate plates relative to each other is advantageously achieved. The bearing bores and the anchoring axis can have any suitable round or angular cross-sectional form. However, a circular cross section of the bearing bores is preferred for the positive-fit arrangement of a rotatable anchoring axis.

If, according to another preferred embodiment, the substrate plates have a rectangular shape and the bearing bore is provided in the corner of the substrate plates, the substrate plates are advantageously are arranged in the stack compound in such a manner that they are arranged in true alignment on top of one another as concerns at least two plate edges. Furthermore, if all substrate plates have the same base area, a straight, compact substrate plate stack with plate edges aligned on all sides is advantageously formed.

A modular construction can be advantageously realized with the substrate of the invention in which construction a plurality of substrate plate stacks are again connected to each other in stacks and/or rows, wherein the compound can again be locked by one or several anchoring axes.

According to an especially advantageous variant of the invention, it can be provided that the bearing bore of at least one of the substrate plates in the stack compound comprises an insertion opening on the edge of the substrate plate through which the bearing bore opens to the circumference of the substrate plate. The provision of the insertion opening means that the bearing bore constitutes a recess formed on the edge of the particular substrate plate. This makes possible a lateral placing or removal of the substrate plate from the anchoring plate without having to remove all the substrate plates axially lined up on the anchoring axis. The insertion opening of the bearing bore thus increases the flexibility when using the substrate of the invention, in which the particular substrate plates can be freely accessed. It is especially preferable if all substrate plates are equipped with the insertion opening on the bearing bore.

Further advantages can result if the insertion opening makes it possible to insert or remove the particular substrate plate only with a predetermined geometric alignment of the substrate plate relative to the anchoring axis. The following measures are provided to this end. The insertion opening forms a collar opening over at least a part of the thickness of the substrate plate which collar opening has a width less than the cross-sectional dimension and especially less than the diameter of the bearing bore. The anchoring axis has such a thickness at least in partial sections that it can be thrust through the collar opening. Partial sections of reduced thickness can be provided on the anchoring axis axially in accordance with the position of the collar opening in the stack direction and/or radially as notched key surfaces. If the substrate plate and the anchoring axis are aligned relatively to one another in such a manner that the collar opening and the partial section with reduced thickness are aligned with one another the substrate plate can be drawn off in a direction vertically to the anchoring axis from the latter.

If, according to another embodiment of the invention, the anchoring axis comprises a protrusion on its upper end, a stop can be formed to fix the substrate plates in the stack compound. The protrusion preferably has a diameter greater than the diameter of the bearing bore in the substrate plates.

According to another variant the anchoring axis is rotatably arranged in the bearing bores. This advantageously makes possible in the first place a suitable alignment of the anchoring axis relative to the collar openings in the stack compound, in the second place it makes it possible to pivot individual substrate plates (see below) and in the third place to fix the anchoring axis by screwing it to a base plate.

According to another advantageous modification of the invention other components can be contained in the substrate plate stack that has other functions than the receiving of samples. For example, at least one data memory device, a base plate and/or a cover plate can be provided that preferably each has the same outer shape as the substrate plates. A data memory can advantageously be integrated in the base plate and/or the cover plate in which information is stored electronically or optically that characterize the substrate and/or the stored samples.

If, according to a preferred embodiment of the invention, the anchoring axis is connected, e.g., by a screw connection, to the lowest substrate plate or the base plate in such a manner that it can be lowered, the substrate plate compound can advantageously be clamped in between the projection at the upper end of the anchoring axis and correspondingly between the lowest substrate plate or the base plate. The state in which all substrate plates are mutually fixed in the stack is also designated as the fix position.

Special advantages for the access to individual substrate plates or individual samples on the substrate plates result if the substrate plates in the stack are pivotal about the anchoring axis. Alternatively or additionally, it can be provided that individual substrate plates can shift perpendicularly to the alignment of the anchoring axis, the substrate plate in this instance being detachable from the compound with the other substrate plates and the anchoring axis. To this end, it is preferably provided that the anchoring axis can be transferred by a rotation from the lowered fix position into a rotary position in which the substrate plates can be moved in accordance with a play in the direction of the stack and can pivot about the anchoring axis, and/or be transferred into a release position in which at least one substrate plate can be separated from the stack.

The stability of the compound of the substrate plates can be increased if, according to another embodiment of the invention, engagement means are provided that prevent a lateral shifting of the substrate plates relative to each other, especially at least in a direction perpendicular to the direction of the stack. For example, profiles can be provided on plane side surfaces of the substrate plates that engage in the substrate compound. The profiles consist, e.g., of nub-shaped protrusions on one plate side and of complementary recesses on the opposing, adjacent plate side. The mutual engagement of such profiles can advantageously be released by loosening the anchoring axis.

According to a modified variant, the engagement means comprise a positive-fit slide guide. The slide guide comprises, e.g., at least one web on a side surface of a substrate plate that cooperates with a groove on a side surface of an adjacent substrate plate. Instead of the engaging webs and grooves on the edges of the side surfaces that are adjacent in the stack, other slide guides such as, e.g., combinations of cylindrical pins with fitting bores or dovetail guides can be provided. The substrate plates can be pushed together and separated from each other like drawers with the slide guides.

Two basic embodiments are distinguished in the realization of the invention. In the first instance, in which the substrate is also designated as a rotary stack substrate, the substrate plates can pivot and, if necessary, also be shifted relative to each other. With the rotary stack substrate, the anchoring axis is a one-piece rod or pin extending over the entire height of the stack consisting of substrate plates (and, as the case may be, of provided additional, plate-shaped components). The rod advantageously has cut surfaces (key surfaces) along its length that make it possible to insert or remove the particular substrate plate for certain alignment relative to the collar openings of the bearing bores. In this instance the anchoring axis advantageously forms the stop for a common alignment of the substrate plates as well as a clamping device for the substrate plate stack.

In the second instance, in which the substrate is also designated as a slide stack substrate, the substrate plates can be exclusively shifted relative to each other. In the slide stack substrate the anchoring axis preferably comprises a plurality of axis segments corresponding to the number of substrate plates (or of additional plate-shaped components) in the substrate stack. The formation of the anchoring axis from a plurality of axis segments has the following particular advantage. The correct length of the anchoring axis is automatically given with the number of substrate plates (or additional components in the stack) that each are equipped with an axis segment.

Each axis segment comprises a cylindrical body with a height corresponding substantially to the thickness of the substrate plates and with a diameter corresponding to the diameter of the bearing bores. Complementary protrusions and recesses are provided on the top and bottom sides of the axis segments that engage in the assembled stack of substrate plates. Individual substrate plates can be drawn out of the compound of the stack or blocked in the stack depending on the alignment of the, e.g., slot-shaped recesses.

Further advantages of the invention regarding the handling of samples can result if the substrate plates each have a compartmental arrangement with a plurality of cup-shaped sample reservoirs. The geometric arrangement of the sample reservoirs can be adapted to the geometric arrangement of micro- or nanotiter plates, as are customary in laboratory technology. Moreover, the substrate plates can each be equipped with an electronic or optical data memory designed to store information about the samples received in the particular substrate plate.

Special advantages for the application of the invention in the cryopreservation result if the substrates consist completely of plastic, e.g., TPX, PE, PTFE, PU or the like. In this instance the parts of the substrates can be economically produced with an injection molding process and subsequently assembled. The stack compound can also be advantageously miniaturized. For example, the substrate plates have side lengths less than 10 cm, preferably smaller than 6 cm.

An important advantage of the invention, that was previously unachieved for substrates for cryopreservation, consists in that the substrate in accordance with the invention can be produced from several components (particularly anchoring axis, substrate plates) of the same or different plastics that ensure sufficient stability and can move relative to each other in all operating states. It surprisingly turned out that the plastics used are relatively soft and deformable at room temperature but nevertheless sufficiently stable. On the other hand, the plastics are hard and non-elastic at the low preservation temperatures, wherein they retain their relative mobility with adapted coefficients of thermal expansion.

As concerns the process, the invention is based on the general technical teaching of storing samples for cryopreservation in a substrate in accordance with the invention with a plate stack and freezing them in the stack compound. The formation of the stack can take place before or after the storing of the samples. The loading of the substrate plates after the formation of the stack can have the advantage that unintended exchange of substrate plates are avoided. The loading of the substrate plates prior to the formation of the stack can have advantages as regards the handling of the substrate plates, e.g., in the laboratory. According to an advantageous variant of the invention individual substrate plates are pivoted and/or pushed in a frozen or thawed state out of the stack compound so that individual samples can be removed in a purposeful manner out of the substrate in accordance with the invention.

Further details and advantages of the invention are apparent from the following description of preferred embodiments.

BRIEF DESCRIPTION OF SEVERAL VIEWS OF THE DRAWINGS

FIGS. 4 and 5 show partial views of substrate plates of a rotary stack substrate from above and below.

FIG. 6 shows a perspective view of an anchoring axis of a rotary stack substrate.

FIGS. 7 and 8 show illustrations of a base element of a rotary stack substrate.

DETAILED DESCRIPTION OF THE PREFERRED EMBODIMENTS

Figure 1:
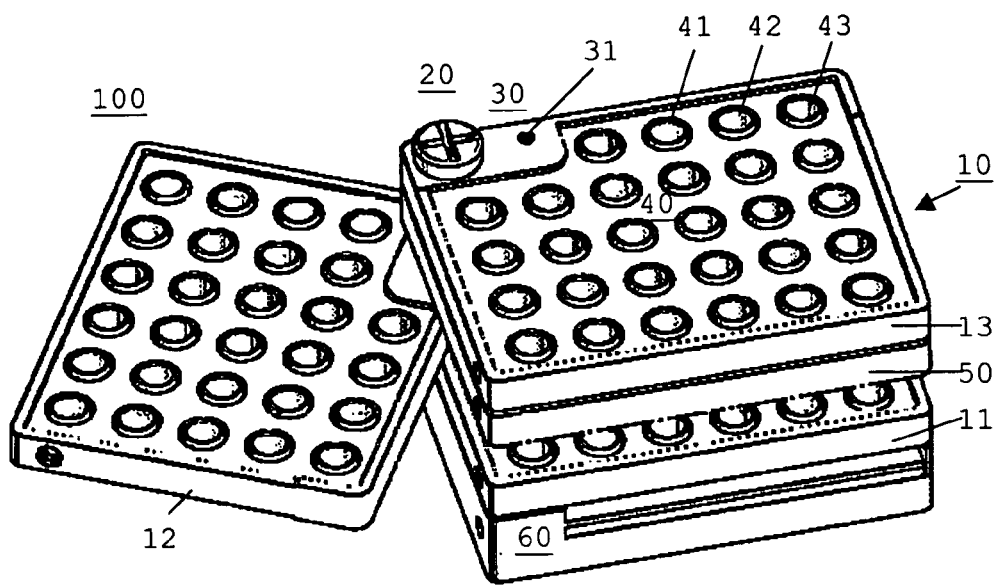
FIGS. 1 to 3 show perspective views of a rotary stack substrate in accordance with the invention.
Figure 2:
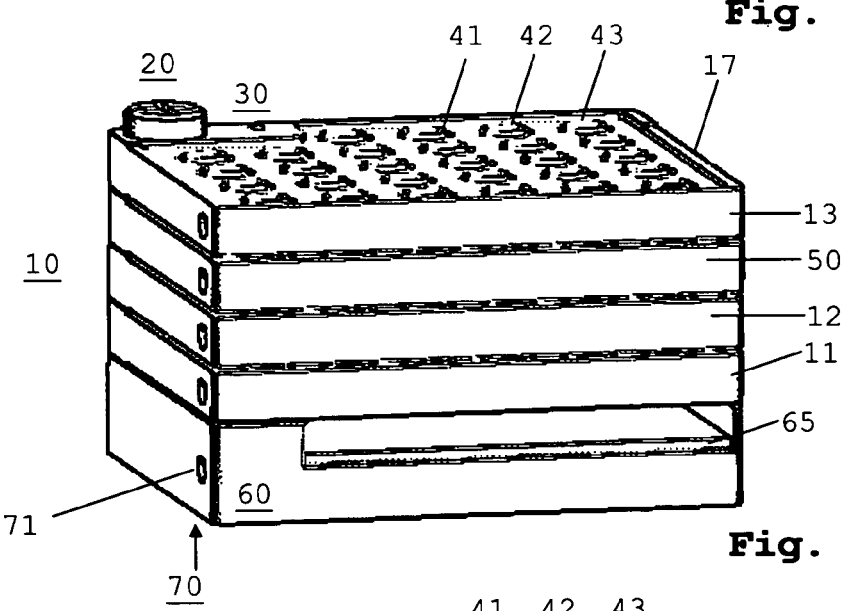
Figure 3:
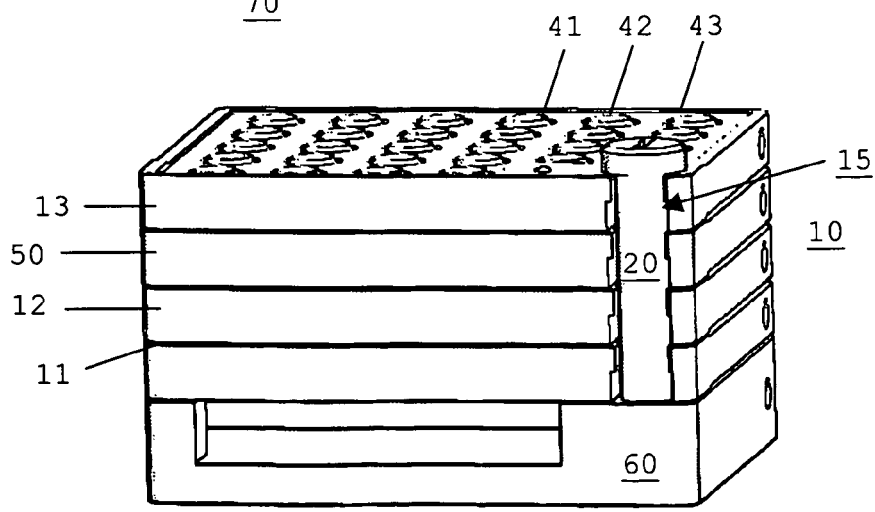

The preferred embodiment of a rotary stack substrate 100 in accordance with the invention shown in FIGS. 1 to 3 comprises a stack 10 made of substrate plates 11, 12, 13 that are connected to each other by an anchoring axis 20 and are arranged on a base element 60. It can be provided that at least one plate in stack 10 comprises an electronic or optical data storage device 50 (e.g., FLASH memory).

Substrate plates 11, 12, 13 are each plane, plate-shaped structural components with a rectangular base form on whose upper side compartmental arrangement 40 is formed with a plurality of sample reservoirs 41, 42, 43. Sample reservoirs 41, 42, 43 are each cup-shaped recesses with a circumferential, circular edge. The upper side of the substrate plates (e.g., 13 in FIG. 2) has a circumferential edge 17 that widens out on at least one side for providing engagement means 30 (see below) and that extends higher over the plate plane than the edges of sample reservoirs 41, 42, 43. For reasons of protection, a protective foil resting on edge 17 can be stretched over the top side of the substrate plates.

Substrate plates 11, 12, 13 are produced from plastic or, as the case may be, from a composite material in which a metal (e.g., aluminum) is embedded. A memory such as, e.g., a magnetic, optical or electronic memory can be integrated (inserted, cast or injected) in at least one of the substrate plates.

Figure 9:
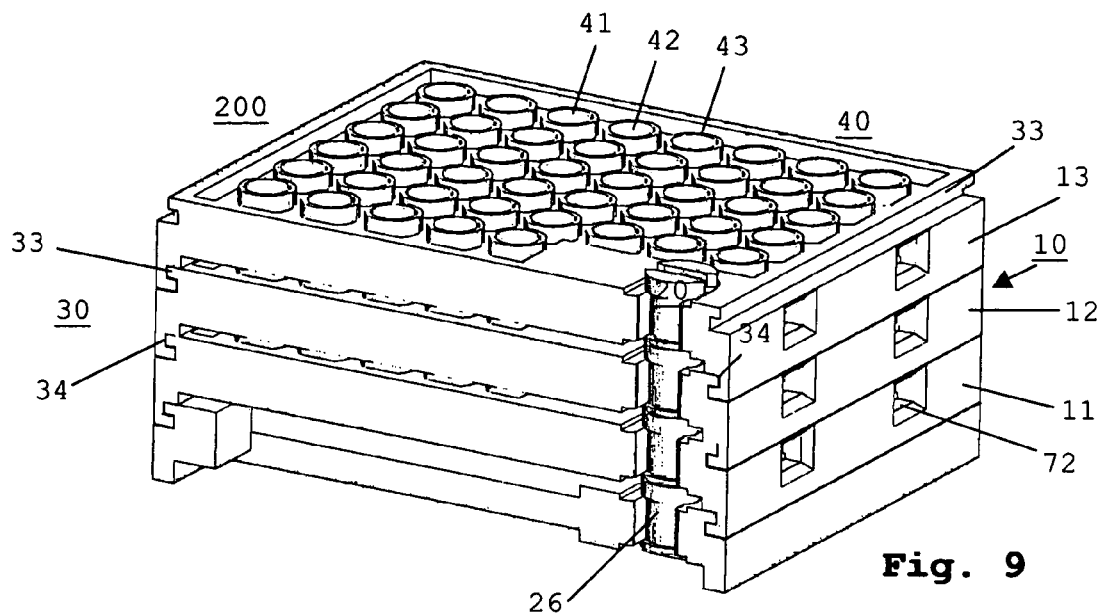
FIG. 9 shows a perspective view of a slide stack substrate in accordance with the invention.

The plates in stack 10 have manipulation openings 70 (e.g., 71 in FIG. 2 or 72 in FIG. 9) on at least one side. The manipulation openings 70 serve to engage manipulation devices, tools or other auxiliary devices with which in particular the transport of the entire substrate or of individual plates is carried out.

The enlarged partial views of substrate plates 11, 12 in FIGS. 4 and 5 show the bearing bore 15 in a corner of the substrate plate which bore opens via insertion opening 16 to the circumference of substrate plates 11, 12. Insertion opening 16 has a collar opening 18 extending over approximately one half the thickness of substrate plate 11 at which opening the width of the gap formed by insertion opening 16 is less than the diameter of bearing bore 15. The collar (the edge of collar opening 18) forms a retention element given a suitable alignment of the anchoring axis relative to the substrate plate (see below).

A nub-shaped protrusion 32 is provided on the lower side of substrate plate 11 (FIG. 4) adjacent to bearing bore 15 as a profile, which protrusion forms engagement means 30 of the rotary stack substrate 100 together with a profile such as, e.g., recess 31 on the adjacent upper side of adjacent substrate plate 12 (FIG. 5).

According to FIG. 6, anchoring axis 20 comprises a continuous rod 21 with a certain outer diameter corresponding to the diameter of bearing bores 15 in the substrate plates and with a projection 22 with a greater diameter. Cut or key surfaces 23 are provided along the length of rod 21 at which the thickness of rod 21 is reduced to the width of collar opening 18 of insertion opening 16. Key surfaces 23 have an axial length that is greater than or equal to the length of collar openings 18 (in the stack direction) and has an axial distance corresponding substantially to the distance of collar openings 18 of the substrate plates in the stack direction.

A threading 24 is provided on the lower end of rod 21. Threading 24 can run over the entire length of anchoring axis 20 so that the latter is designed as a screw. This design makes possible a simple cutting to size of the desired length of an anchoring axis. A slot 25 is provided on the upper end of rod 21 in projection 22. Anchoring axis 20 consists of plastic or, as the case may be, of a composite material of plastic in which a metallic core (e.g., of aluminum) is embedded.

The base plate 60 shown in FIG. 7 forms a lowest carrier for stack 10 of substrate plates 11, 12, 13. The base plate 60 comprises a threaded bore 61 on its upper side that is aligned in accordance with the position of bearing bores 15 and is designed to receive threading 24 of anchoring axis 20. Furthermore, recess 62 is provided on the top side of base plate 60 in analogy with recess 31.

Figure 12:
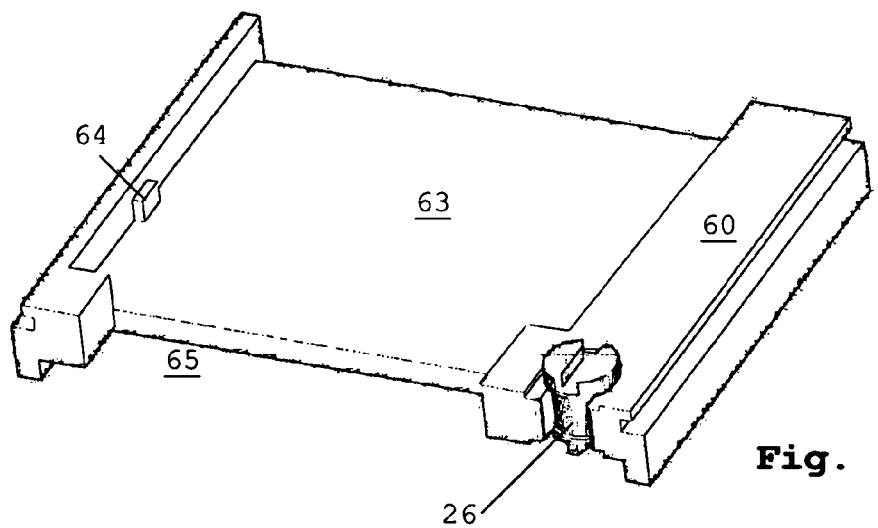
FIG. 12 shows a base element of a slide stack substrate.

The base plate 60 has a recess 63 for receiving a magnetic, electronic or optical data memory (not shown). The data memory is inserted in recess 63 and fixed by protrusions 64 on the edges of recess 63. Alternatively, the data memory can be cast in or injected in. Recess 63 has at least one lateral opening parallel to the plate plane through which on the one hand the data memory can be inserted even when the stack is assembled and through which on the other hand an electrical connection for the data memory can be run. Thus, reference sign 65 refers to an interface opening (see also FIG. 12). If the data memory is formed, e.g., by a compact FLASH memory, a plug with contact pins for connection to the compact FLASH memory can be inserted through interface opening 65 and, as the case may be, laterally fixed at least temporarily to the base plate (e.g., with a clip connection). The data memory can be connected via the interface to an external control device.

The attaching of the data memory described using the example of base plate 60 can also be provided on at least one of the substrate plates or the cover plate.

FIG. 8 illustrates the first step in the construction of a rotary stack substrate 100 in accordance with the invention. At first, anchoring axis 20 is loosely screwed into base element 60 so that key surfaces 23 stand vertically to insertion opening 16. In this raised state, that is also designated as the release position, key surfaces 23 are located along the length of the anchoring axis at such a height above the base plate that the collar openings (18) of the substrate plates in the stack are aligned with key surfaces 23. In the release position the anchoring axis can be inserted through the insertion openings 16 into the bearing bore or pushed out of it. In the release position the lowest substrate plate 11, which is possibly already loaded with samples, is pushed onto base plate 60. Since the lowest key surface 23 is appropriately aligned, substrate plate 11 can be pushed forward until anchoring axis 20 runs through bearing bore 15. Other substrate plates are subsequently pushed on in accordance with the length of anchoring axis 20 used.

Anchoring axis 20 is at first still in the raised state of the release position after the completion of stack 10. Anchoring axis 20 is lowered by rotating the anchoring axis, e.g., with a screwdriver that engages into slot 25 of projection 22 (see FIG. 6). When anchoring axis 20 is screwed into base plate 60, the alignment of key surfaces 23 with collar openings 18 is lost along the length of anchoring axis 20. Substrate plates 11, 12, 13 can no longer be separated from stack 10. During the screwing in, a state is at first reached in which substrate plates 11, 12, 13 between projection 22 of anchoring axis 21 and base plate 60 still have play in the direction of the stack and can slightly move. This state is also designated as the rotary position of anchoring axis 20. In the rotary position the play of substrate plates 11, 12, 13 is greater than the height of profiles 31, 32 so that substrate plates 11, 12, 13 can be pivoted out of the stack around anchoring axis 20.

In order to lock the stack compound, the anchoring axis 20 is firmly screwed into base plate 60. This state is also designated as the fix position of anchoring axis 20. In the fix position the substrate plates are pressed together so that engagement means 31, 32 engage and block a further shifting or pivoting of the substrate plates.

The freezing and storage of substrate 100, e.g., at the temperature of liquid nitrogen or in the vapor of liquid nitrogen (normal pressure) can take place in the fix position. If individual samples are to be removed such as, e.g., from substrate plate 12 according to FIG. 1, the anchoring axis 20 can be transferred into the rotary position by loosening the screw connection to base plate 60. In this state engagement means 31, 32 is released so that substrate plate 12 can pivot laterally outward about anchoring axis 20 (FIG. 1). The rotation of anchoring axis 20 and/or of substrate plate 12 can be selected in such a manner that the key surfaces 23 appropriately cooperate with insertion openings 16 so that substrate plate 12 can be separated from stack 10. For example, 1 to 20 substrate plates are arranged on top of one another in rotary stack substrate 100. An anchoring axis 20 with a suitable length is used as a function of the desired number of plates.

FIG. 8 shows the anchoring axis in the fix position for purposes of illustration although the stack has not yet been completed.

The invention has the particular advantage that the anchoring axis can be adjusted between the release, rotary and fix positions solely by a rotation, e.g., by the screwing into the base plate. The raising during screwing is determined by the pitch of the threading 24. In this manner, the transfer between the different positions can be advantageously set by the number of revolutions of the anchoring axis.

In general, preferably at least one information carrier is provided on a substrate stack that is formed by the above-indicated data memories and/or by additional storage media such as, e.g., a barcode.

A preferred embodiment of a slide stack substrate 200 is illustrated in FIGS. 9 to 12. In slide stack substrate 200 engagement means 30 is designed as a positive-fit slide guide consisting, e.g., of webs 33 and grooves 34 that are formed as straight guide rails complementary to each other on the edges of the top and the bottom of the substrate plates. In the stack webs 33 of a substrate plate reach behind grooves 34 of the adjacent substrate plate so that the stack is formed by successively pushing on the substrate plates. A one-piece anchoring axis 20 with key surfaces 23 can also be provided in this variant in order to prevent a further shifting of the substrate plates after stack 10 has been completed.

However, an anchoring axis 20 formed from axis segments 26 is preferably used in the slide stack substrate. This has the advantage that the length of anchoring axis 20 can easily be adjusted by the number of axis segments 26 used corresponding to the number of substrate plates.

Figure 10:
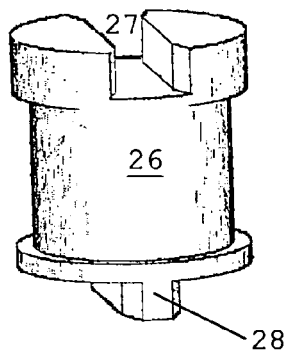
FIG. 10 shows an enlarged representation of an axis segment.

According to FIG. 10 each axis segment 26 comprises a cylindrical body on whose top and bottom complementary, slot-shaped recesses 27 and protrusions 28 are formed. In the assembled slide stack substrate 200 a protrusion 28 engages into the recess 27 of axis segment 26 underneath it. If the alignment of the slot-shaped recesses and protrusions 27, 28 runs parallel to the alignment of engagement means 33, 34, substrate plates can be separated from each other by pushing them in the direction of the joint. If the slot-shaped recesses and protrusions 27, 28 have a different alignment the mutual shifting of the substrate plates is blocked.

Figure 11:
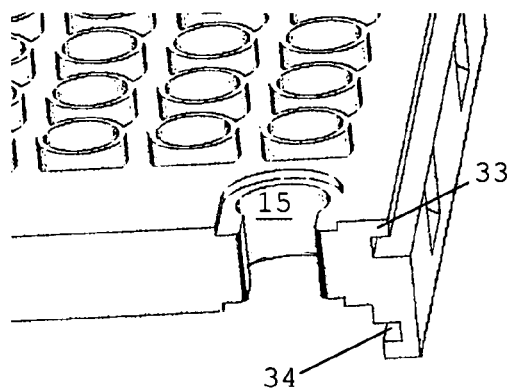
FIG. 11 shows a partial view of a substrate plate in a slide stack substrate.

The axis segments 26 are rotatably arranged in bearing bores 15 (see FIG. 11). The substrate plates are preferably prefabricated with the axis segments. During the prefabrication, the axis segments are pressed at room temperature into the bearing bores of the substrate plates. The axis segments 26 can hardly be removed from bearing bores 15 any more without being destroyed at the operating temperature of cryo-preservation, at which the elasticity of the materials is greatly limited.

A base element 60 (FIG. 12) is also provided in slide stack substrate 200 in which part an axis segment 26 is appropriately arranged.

The substrate plates and anchoring axes of substrate 100, 200 are preferably manufactured by injection casting from TXP, PE, PTFE or the like. The side lengths of the substrate plates are, e.g., in a range of 10 mm to 20 cm or more such as, e.g., 50 cm or 80 cm. The thickness of the substrate plates is, e.g., 4 mm to 5 cm or more. The number of sample reservoirs 41, 42, 43 per substrate plate is a function of the size of the substrate plate and of the sample reservoir and is, e.g., 20 to 200 for rather small formats. In the case of larger formats, the number can be considerably higher and be, e.g., 5,000 to 10,000.

The size and form of the sample reservoirs are a function of the biological samples (especially biological tissue, tissue parts, biological cells, cell groups, cell components, cellular organelles or biologically relevant macromolecules) that are to be stored.

In distinction to the embodiments shown, modifications, especially as concerns the geometry of the individual parts, can be provided depending on the requirements when using the substrate of the invention. For example, it is not necessary, according to the invention, that all substrate plates have the same base area but rather substrate plates with different base areas can be combined in the stack. For example, the base area can become smaller toward the top in the stack. Furthermore, it is not obligatorily provided that the anchoring axes and bearing bores have a round cross section. An anchoring axis with an angular cross section can also be provided. Finally, the key surfaces can be aligned differently relative to each other in the rotary stack variant so that during the rotation of the anchoring axis one substrate plate is released at a time and the others blocked.

The features of the invention disclosed in the specification, the drawings and the claims can be significant individually or in combination for the realization of the invention in its various embodiments. In particular, the features described for the rotary stack substrate can be provided in the slide stack substrate (or vice versa).

The invention claimed is:

1. A substrate for receiving and cryopreserving a plurality of samples, said substrate comprising:
   a plurality of substrate plates arranged on top of one another as a stack, and
   an anchoring axis, to which the substrate plates are connected,
   wherein: (a) each substrate plate has a compartmental arrangement with a plurality of sample reservoirs and a bearing bore through which the anchoring axis passes, (b) in an assembled state of the substrate the substrate plates can pivot out of the stack about the anchoring axis, and (c) at least one of the substrate plates is adapted to be laterally removed from the anchoring axis without removing all of the remaining substrate plates connected to the anchoring axis.

2. The substrate according to claim 1, wherein the substrate plates have a rectangular shape and the bearing bore is in each case provided in a corner of the substrate plates.

3. The substrate according to claim 1, wherein the bearing bore of at least one of the substrate plates has an insertion opening on an edge for the lateral insertion of the anchoring axis into the bearing bore.

4. The substrate according to claim 3, wherein the insertion opening forms a collar opening with a lesser width, relative to a diameter of the bearing bore, and the anchoring axis has a thickness at least in partial sections of its length that is smaller than or equal to the width of the collar opening.

5. The substrate according to claim 1, wherein the anchoring axis has a projection on its upper end.

6. The substrate according to claim 1, wherein the anchoring axis is rotatably arranged.

7. The substrate according to claim 1, wherein the stack contains at least one of a data storage device, a base plate and a cover plate.

8. The substrate according to claim 7, wherein the base plate contains a data memory.

9. The substrate according to claim 7, wherein the anchoring axis is detachably connected to a lowest substrate plate or to the base plate.

10. The substrate according to claim 1, wherein at least one substrate plate in the stack can be shifted vertically to the anchoring axis.

11. The substrate according to claim 1, wherein the substrate plates comprise engagement means that block a lateral shifting of the substrate plates at least in a direction vertically to a stack direction.

12. The substrate according to claim 11, wherein the engagement means comprise at least one profile on a lateral surface of a substrate plate that cooperates with a complementary profile on a lateral surface of an adjacent substrate plate.

13. The substrate according to claim 11, wherein the anchoring axis can be transferred by a rotation from a lowered fix position, in which all substrate plates in the stack are mutually fixed, into a rotary position, in which the substrate plates can be moved in accordance with a play in a direction of the stack and pivot about the anchoring axis, and/or be transferred into a release position in which at least one substrate plate can be separated from the stack.

14. The substrate according to claim 11, wherein the engagement means are formed by a positive-fit slide guide.

15. The substrate according to claim 1, wherein the anchoring axis comprises a one-piece rod extending over a height of the stack.

16. The substrate according to claim 4, wherein the anchoring axis comprises a one-piece rod extending over a height of the stack, and the rod has key surfaces that form the partial sections with the thickness that is smaller than or equal to the width of the collar opening.

17. The substrate according to claim 1, wherein the anchoring axis comprises a plurality of axis segments.

18. The substrate according to claim 17, wherein the axis segments each comprise a cylindrical body with a height corresponding substantially to a thickness of the substrate plates and with a diameter corresponding to a diameter of the bearing bores, complementary recesses and protrusions being provided on the top and bottom sides of the axis segments that engage into each other in the assembled stack of substrate plates.

19. The substrate according to claim 1, wherein at least one substrate plate contains a data memory.

20. The substrate according to claim 1, wherein the substrate plates comprise plastic.

21. The substrate according to claim 1, wherein the substrate plates have side lengths less than 10 cm.

22. A process for the cryopreservation of samples with a substrate according to claim 1, with the steps:
   storage of the samples on the substrate plates, and
   freezing of the substrate plates in the stack.

23. The process according to claim 22, wherein the stack of substrate plates is formed before the storage of the samples.

24. The process according to claim 22, wherein the stack of substrate plates is formed after the storage of the samples.

25. The process according to claim 22, wherein individual substrate plates are pivoted or pushed out of the stack in a frozen or thawed state.

26. The process of claim 22, wherein the samples are liquids or particulates.

27. The process of claim 22, wherein the samples are biological samples.

* * * * *